United States Patent
Newman

[11] Patent Number: 5,921,242
[45] Date of Patent: Jul. 13, 1999

[54] DRAPE SHEETS FOR USE IN SURGICAL PROCEDURES

[75] Inventor: Charles L. Newman, Stillwater, Minn.

[73] Assignee: 3M Innovative Properties Company, St. Paul, Minn.

[21] Appl. No.: 08/851,910

[22] Filed: May 6, 1997

[51] Int. Cl.[6] .................................................. A61B 19/00
[52] U.S. Cl. ........................................... 128/849; 128/855
[58] Field of Search ................................. 128/849–856

[56] References Cited

U.S. PATENT DOCUMENTS

| | | | |
|---|---|---|---|
| 3,030,957 | 4/1962 | Melges | 128/292 |
| 3,037,507 | 5/1962 | Melges | 128/292 |
| 3,335,719 | 8/1967 | Boucher | 128/132 |
| 3,343,534 | 9/1967 | Keoughan, Jr. et al. . | |
| 3,424,153 | 1/1969 | Lewis, Jr. | 128/132 |
| 3,494,356 | 2/1970 | Melges | 128/132 |
| 3,537,446 | 11/1970 | Roland, Jr. et al. | 128/132 |
| 3,540,441 | 11/1970 | Collins | 128/132 |
| 3,613,676 | 10/1971 | Endres et al. | 128/132 |
| 3,667,458 | 6/1972 | Krebs | 128/132 |
| 3,693,618 | 9/1972 | Madden | 128/132 |
| 3,695,260 | 10/1972 | Endres | 128/132 |
| 3,707,964 | 1/1973 | Patience et al. | 128/132 |
| 3,721,234 | 3/1973 | Hadtke et al. | 128/132 |
| 3,741,206 | 6/1973 | Bimard et al. | 128/132 |
| 3,750,663 | 8/1973 | Collins | 128/132 |
| 3,769,971 | 11/1973 | Collins | 128/132 |
| 3,777,749 | 12/1973 | Collins | 128/132 |
| 3,791,381 | 2/1974 | Krzewinski . | |
| 3,809,077 | 5/1974 | Hansen | 128/132 |
| 3,878,843 | 4/1975 | Morgan | 128/132 |
| 3,881,476 | 5/1975 | Bolker et al. . | |
| 3,910,268 | 10/1975 | Miller | 128/132 |
| 3,934,582 | 1/1976 | Gorrie | 128/157 |
| 3,968,792 | 7/1976 | Small | 128/132 |
| 3,989,040 | 11/1976 | Lofgren et al. | 128/132 |
| 3,998,221 | 12/1976 | Collins | 128/132 |
| 4,027,665 | 6/1977 | Scivens | 128/132 |
| 4,051,845 | 10/1977 | Collins | 128/132 |
| 4,153,054 | 5/1979 | Boone | 128/132 |
| 4,164,941 | 8/1979 | Knopick et al. | 128/132 |
| 4,354,486 | 10/1982 | Oliver | 128/132 |
| 4,457,026 | 7/1984 | Morris | 2/171 |
| 4,479,492 | 10/1984 | Singer . | |
| 4,522,203 | 6/1985 | Mays | 128/132 |
| 4,553,539 | 11/1985 | Morris . | |
| 4,593,418 | 6/1986 | Simon | 2/275 |
| 4,596,244 | 6/1986 | Jackson | 128/132 |
| 4,627,427 | 12/1986 | Arco | 128/132 |
| 4,683,593 | 8/1987 | Langley | 2/82 |
| 5,586,563 | 12/1996 | Newman | 128/849 |

FOREIGN PATENT DOCUMENTS 2 227 845  11/1974  France .

Primary Examiner—Michael A. Brown
Attorney, Agent, or Firm—Gary L. Griswold; Eloise J. Maki; Stephen W. Bauer

[57] ABSTRACT

A sheet drape is folded first in one direction into a multilayer strip of material and then in the orthogonal direction into a stack with a first end of the multilayer length located on top of the stack and the second end located within the stack. The drape is unfolded by pulling the first end of the multilayer length in a first direction, to reveal the second end; pulling the second end in the second, opposite, direction (thereby returning to the form of the multilayer strip); and then opening the folds of the multilayer strip.

18 Claims, 5 Drawing Sheets

DRAPE SHEETS FOR USE IN SURGICAL PROCEDURES

The present invention relates to surgical drapes and, in particular, to drape sheets. The invention relates more especially, but not exclusively, to drape sheets for use on tables and is concerned with the method of use of such drapes and the form in which such drapes are supplied for use in operating theaters.

BACKGROUND OF THE INVENTION

The use of surgical drapes in operating theaters is well established. Drapes are employed to cover, and to separate, non-sterile objects (for example, the non-sterile parts of a patient's body) from the sterile environment of the operating theatre and the operating theatre staff, and are available in many different shapes and constructions, depending on the nature of the surgical procedure that is being carried out. Increasingly, drapes are intended for a single use only and are supplied to users already sterilized, in sterile packaging. Usually, it is necessary for the drapes to be folded so that the packages are of a convenient shape and size and it is then necessary to ensure that, in the operating theatre, it is possible to unfold and place the drape in position without contaminating the outer surface of the drape material (e.g., in the case of a patient drape, the surface remote from the patient's body and, in the case of a table drape, the surface remote from the surface of the table). In other words, it is necessary to ensure that the drape can be unfolded and placed in position without the outer surface of the drape material coming into contact with non-sterile objects (for example, the patient's body) because the surface will then no longer be aseptic (uncontaminated). It is also desirable that it should be possible to unfold and position a drape quickly and easily, to avoid introducing delays.

Sheet drapes, comprising rectangles of drape material, are widely used during surgical procedures for covering areas of the patient's body and also for covering flat surfaces (e.g. instrument tables) in the operating theatre. Sheet drapes are available in a wide range of sizes and the larger sizes can present particular problems both for the supplier, in that they have to be folded many times before they are of a convenient size for packaging, and for the user, in that they have to be handled carefully to avoid contamination.

The importance of the way in which drapes are folded is well recognised, and various ways of folding particular drapes have been proposed. One known way of folding sheet drapes comprises fan-folding the drape in the longitudinal direction from the ends to the middle, forming an elongated multi-layer strip, and then in the transverse direction from the sides (now the ends of the multi-layer strip) to the middle. The result is two side-by-side stacks of fan-folded material, each having a respective edge of the drape on top and joined at the bottom by a bridging portion. The bridging portion is then folded in half, to form a single stack of folded material with the bridging portion on the outside faces.

A sheet drape which has been folded by that method is compact and, from the point of view of a drape supplier, has the advantage that it is very suitable for packaging. The folding method has the disadvantage, however, that a comparatively large number of steps are involved in fan-folding the drape in the two directions. From the point of view of the user there is the advantage that, when the bridging portion has been unfolded to reveal the two side-by-side stacks of folded material, the side edges of the drape are immediately accessible for unfolding the drape in a comparatively simple manner. The need to unfold the bridging portion first can, however, present problems since it requires the user to locate the center of the single stack formation in which the drape is supplied. In addition, if there are a comparatively large number of fan-folds to be undone, it can be difficult for the user (especially when working single-handed) to control the drape during the unfolding operation.

Various methods of folding sheet drapes, or other drapes having a sheet-like form, are described in U.S. Pat. Nos. 3,343,534; 3,537,446; 3,721,234; 4,051,845; 4,164,941; 4,553,539; and 4,627,427.

SUMMARY OF THE INVENTION

The present invention is concerned with enabling a sheet drape to be folded comparatively simply but in such a way that it is comparatively easy for a user to apply without undue risk of the drape being contaminated by contact with non-sterile surfaces.

The invention provides a surgical drape comprising a rectangular sheet of drape material folded, prior to use, in one direction to form a multi-layer strip of material having first and second ends, and then in the orthogonal direction to form a stack of folded material with the first end of the multi-layer strip exposed at the top of the stack, wherein at least one of the folds in the orthogonal direction extends through more than one thickness of the multi-layer strip.

The present invention further provides a surgical drape comprising a rectangular sheet of drape material folded, prior to use, in one direction to form a multi-layer strip of material having first and second ends, and then in the orthogonal direction to form a stack of folded material with the first end of the multi-layer strip exposed at the top of the stack and the second end located within the stack, wherein the folds in the orthogonal direction allow a first part of the stack to be unfolded, to expose the second end, by pulling the first end in a first direction.

The present invention also provides a method of folding a rectangular surgical drape comprising the steps of:

folding the drape in one direction to form a multi-layer strip of material having first and second ends; and folding the multi-layer strip in the orthogonal direction to form a stack of folded material with the first end of the multi-layer strip exposed at the top of the stack, wherein at least one of the folds in the orthogonal direction extends through more than one thickness of the multi-layer strip.

The present invention further provides a method of folding a rectangular surgical drape comprising the steps of:

folding the drape in one direction to form a multi-layer strip of material having first and second ends; and folding the multi-layer strip in the orthogonal direction to form a stack of folded material with the first end of the multi-layer strip exposed at the top of the stack and the second end located within the stack, wherein the folds in the orthogonal direction allow a first part of the stack to be unfolded, to expose the second end, by pulling the first end in a first direction.

In accordance with the invention, there is also provided a method of using a surgical drape, comprising the steps of:

providing a surgical drape comprising a rectangular sheet of drape material folded in one direction to form a multi-layer strip of material having first and second ends, and then in the orthogonal direction to form a stack of folded material with the first end of the multi-layer strip exposed at the top of the stack and the second end located within the stack;

placing the folded drape on a surface to be covered;

unfolding a first part of the stack, to expose the second end of the multi-layer strip, by pulling the first end in a first direction;

unfolding the remainder of the stack by pulling the second end in a second direction opposite to the first direction; and unfolding the multi-layer strip of material in directions perpendicular to the first and second directions.

BRIEF DESCRIPTION OF THE DRAWINGS

By way of example only, embodiments of the invention will be described with reference to the accompanying drawings, in which.

DETAILED DESCRIPTION OF PREFERRED EMBODIMENTS

Figure 1:
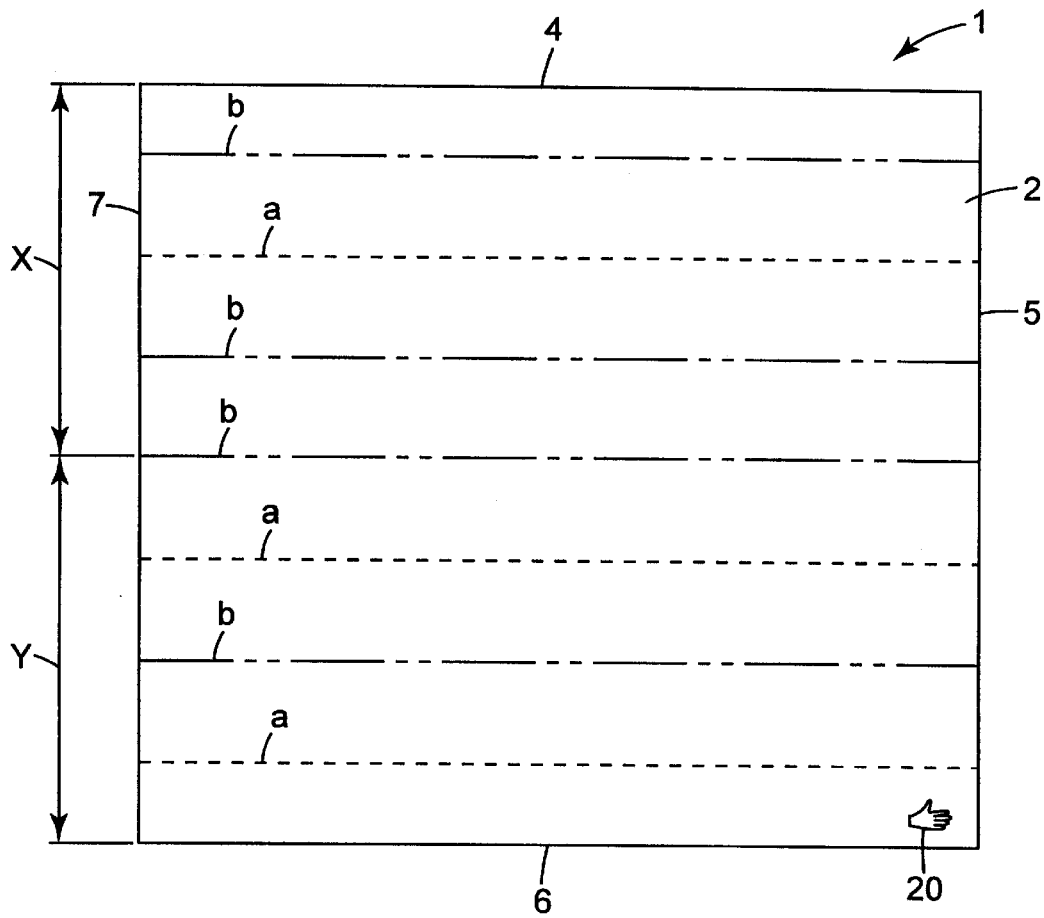
FIG. 1 is a plan view of a sheet drape in an unfolded condition.

FIG. 1 shows a sheet drape 1 for use in covering a table in an operating theatre to provide a sterile surface on which sterile items such as surgical instruments can be placed during a surgical procedure. The drape 1 comprises a rectangle of any suitable drape material. In the case of a disposable drape (i.e. a drape intended for a single use only) the material may comprise a fluid-impervious layer (for example, a plastic film) to which is laminated a fluid absorbent layer (for example, a non-woven layer), or alternatively a single layer fluid-impervious film drape. The plastic film may, for example, be a polyethylene or a polypropylene film and the non-woven layer may, for example, be a polypropylene spun-bond material, melt-blown material or a hybrid melt-blown/spun bond material. Most preferably, a polyethylene film is extruded onto the polypropylene spun-bond layer. Drape materials are disclosed in U.S. Pat. Nos. 5,586,563 and 3,809,077 (disclosing a three-layer structure: non-woven/film/non-woven), which are incorporated herein by reference.

An alternative material for a disposable drape is a non-woven material that has been chemically-treated to make it fluid repellent. If the drape 1 is a reusable drape, it may be formed of a woven cotton or linen material, which may be treated to make it fluid repellent.

The drape 1 comprises an upper surface 2 (which is the surface shown in FIG. 1) and a lower surface 3 (not visible in FIG. 1), which, when the drape is in use, is the surface adjacent the table. The four edges of the drape 1 are indicated in FIG. 1 by the reference numerals 4, 5, 6 and 7, the edges 4 and 5 being opposite the edges 6 and 7 respectively. The corner formed by the edges 5 and 6 carries a distinctive marking 20 (shown as a hand) the purpose of which will be described below.

Drapes are normally supplied folded, the extent of the folding being dependent in each case on the size of the drape. Disposable drapes are normally supplied folded in sterile packaging and may be packaged individually or with other similar drapes or as part of a set of different drapes. When a sheet drape as shown in FIG. 1 is used to cover a table, it is important that the person applying the drape should be able to unfold it and spread it over the table without contacting the table (which is non-sterile). It is also important that the upper surface 2 of the drape does not contact the table, or any other non-sterile surface. To assist in applying the sheet drape, it is folded in the following manner.

Figure 2:
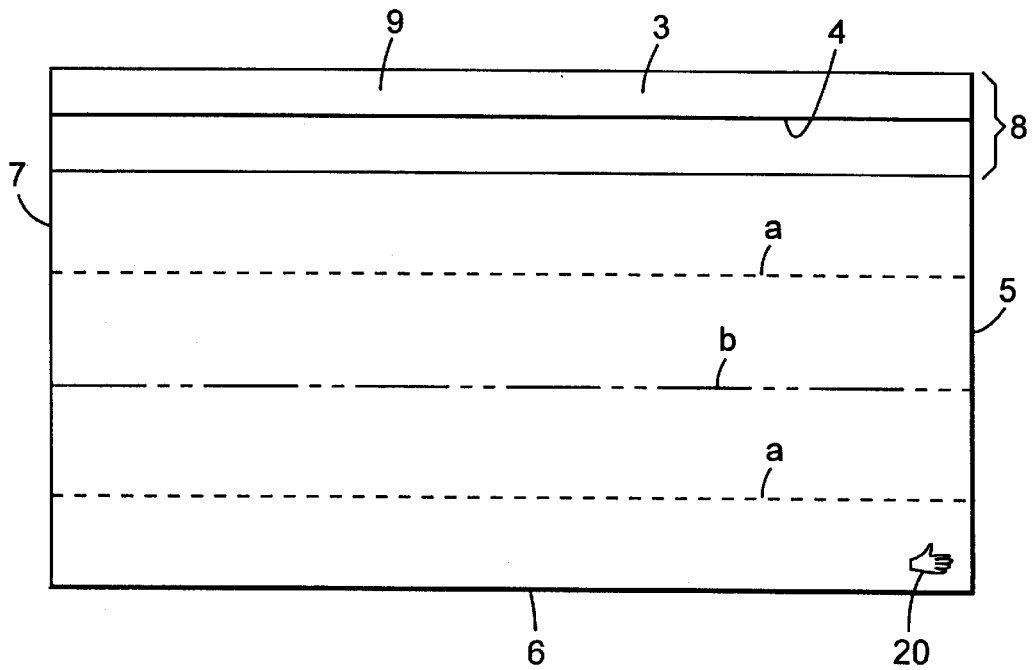
FIGS. 2 and 3 are similar views, showing the drape after first and second folding steps, respectively.

Starting from the edge 4 of the drape 1, a portion of the drape indicated by "X" in FIG. 1 is fan-folded towards the central region of the drape, forming a strip 8 of folded material as shown in FIG. 2. The fold lines are generally parallel to the edges 4, 6 and the directions of the folds are such that the edge 4 is positioned at the top of the strip 8 with its direction reversed (so that it is now directed towards the edge 6). The top layer of the strip 8 is not as wide as the remainder of the strip 8 and forms a flap 9 which later assists a user in unfolding the drape, as will be described below. Consequently, part of the lower surface 3 of the drape 1 is now visible, adjacent the edge 4, on the top of the stack 8 and is shown shaded in FIG. 2.

Figure 3:
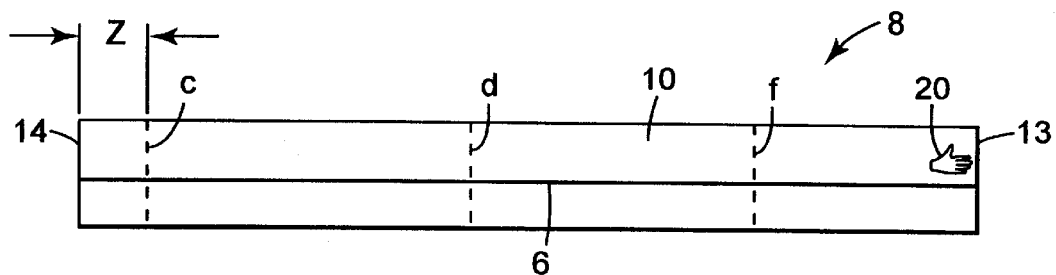
Figure 4:
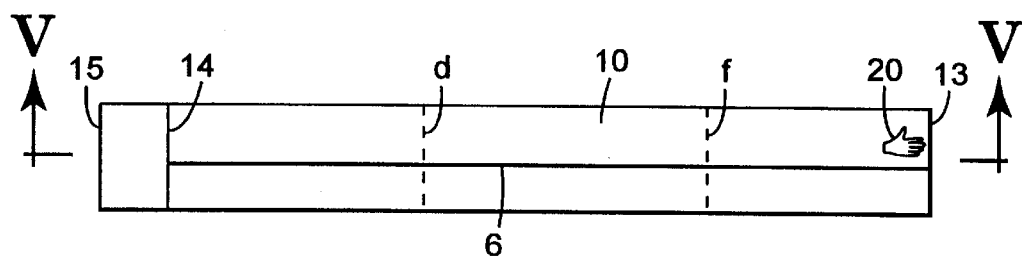
FIG. 4 is a plan view showing the drape after a third folding step.
Figure 5:
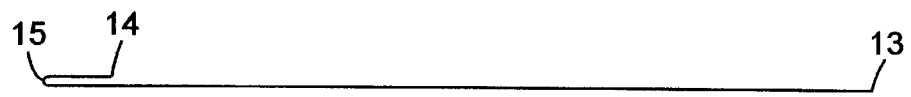
FIG. 5 is a diagrammatic cross-section on the line V—V in FIG. 4.

The remainder of the drape (indicated by "Y" in FIG. 1) is now fan-folded, from the edge 6, onto the top of the strip 8 as shown in FIG. 3. The fold lines are again generally parallel to the edges 4, 6 and position the edge 6 at the top of the strip 8, this time with the direction of the edge unchanged. The new top layer of the strip 8 is also not as wide as the remainder of the strip and again forms a flap 10 which later assists a user in unfolding the drape, as will be described below.

The fan-folds which bring the drape to the form shown in FIG. 3 are indicated as dotted and broken lines in FIGS. 1 and 2, the dotted lines a indicating folds in one direction and the broken lines b indicating folds in the other direction.

The strip 8 into which the drape 1 has been folded is effectively a multilayer strip (also 8) of material the ends 13 and 14 of which correspond to the edges 5 and 7 of the drape. The remainder of the folding procedure comprises folding the multi-layer strip 8 into twelve sections, at right angles (i.e. the "orthogonal direction") to the fan-folds a, b, by the steps illustrated in FIGS. 4 to 14 (in which a single thickness of the multi-layer strip is depicted, for clarity, by a single line). Those folding steps are as follows:

(i) The end 14 of the multi-layer strip 8 is folded over along a line c (FIG. 3) at a distance Z from the end 14 (where Z is equal to approximately one twelfth of the distance between the ends 13, 14). The multi-layer strip 8 now has the form shown in FIGS. 4 and 5.

Figure 6:
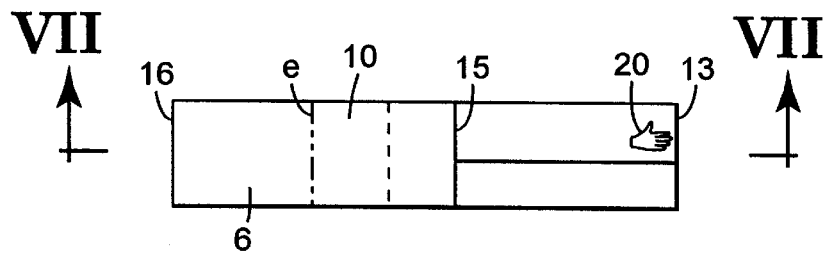
FIG. 6 is a plan view showing the drape after a fourth folding step.
Figure 7:
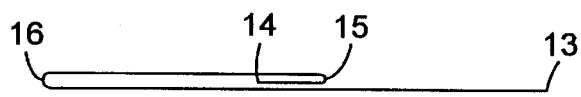
FIG. 7 is a diagrammatic cross-section on the line VII—VII in FIG. 6.

(ii) The folded end 15 of the multi-layer strip 8 is folded over along a line d (FIG. 4) at a distance about 4Z from the folded end 15, bringing the multi-layer strip into the form shown in FIGS. 6 and 7.

(iii) The extreme folded end 16 of the multi-layer strip 8 is folded over along a line e (FIG. 6) at a distance about 2Z from the end 16. This fold, which extends through two thicknesses of the multi-layer strip 8, locates the folded end 16 on top of the folded end 15 and brings the multi-layer strip into the form shown in FIGS. 8 and 9.

Figure 10:
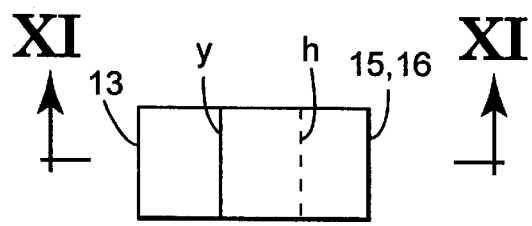
FIG. 10 is a plan view showing the drape after a sixth folding step.
Figure 11:
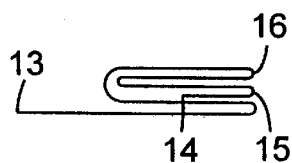
FIG. 11 is a diagrammatic cross-section on the line XI—XI in FIG. 10.

(iv) The end 13 of the multi-layer strip 8 is folded under along a line f (FIG. 8) aligned with the folded ends 15, 16, bringing the multi-layer strip into the form shown in FIGS. 10 and 11.

Figure 12:
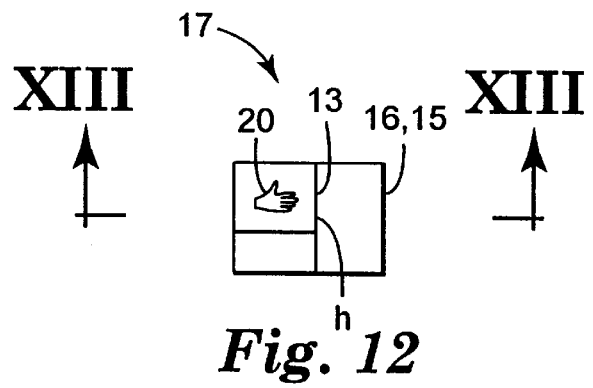
FIG. 12 is a plan view showing the drape after a seventh folding step.
Figure 13:
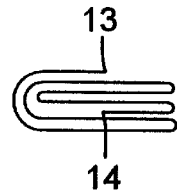
FIG. 13 is a diagrammatic cross-section on the line XIII—XIII in FIG. 12.

(v) The end 13 of the multi-layer strip 8 is folded over along a line g (FIG. 10) at a distance about Z from the end, forming a stack 17 of folded material as shown in FIGS. 12 and 13. The end 13 is located approximately on the vertical centre line h of the stack.

Figure 14:
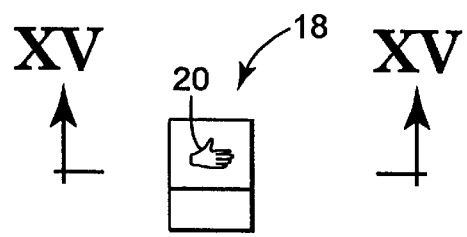
FIG. 14 is a plan showing the drape in its folded form.
Figure 15:
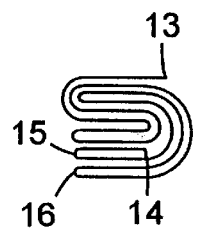
FIG. 15 is a diagrammatic cross-section on the line XV—XV in FIG. 14.

(vi) The stack 17 is folded in half on the vertical centre line h (FIG. 12), leaving the end 13 on the top, to form a stack 18 as shown in FIGS. 14 and 15. The end 13 of the multi-layer strip 8 is approximately aligned with one side of the stack 18. The end 14 of the multi-layer strip 8 is located within the stack 17 and approximately aligned with the same side of the stack as the end 13.

Figure 7A:
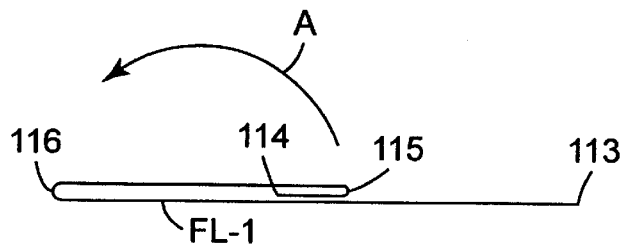
FIG. 7A is a diagrammatic cross-section similar to FIG. 6 illustrating a preferred step that brings the drape into the folded state shown in FIG. 11 and 11A.
Figure 8:
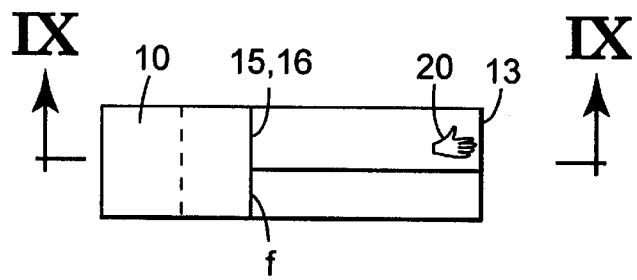
FIG. 8 is a plan view showing the drape after a fifth folding step.
Figure 9:
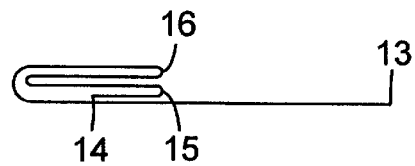
FIG. 9 is a diagrammatic cross-section on the line IX—IX in FIG. 8.
Figure 11A:
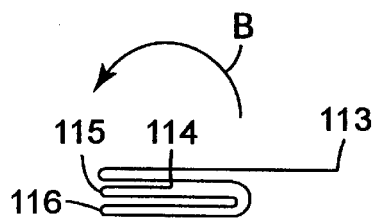
FIG. 11A is a diagrammatic cross-section similar to FIG. 11 illustrating a preferred step that brings the drape into the folded form shown in FIGS. 14 and 15.

FIGS. 7A and 11A illustrate a preferred folding method that consolidates four of the folding steps described above into two steps. The reference numerals used in FIGS. 7A and 11A equal the reference numerals used in FIGS. 7 and 11 plus 100. The multi-layer strip is folded into the form shown in FIGS. 7 and 7A. Then, folded edge 115 is folded over a fold line FL-1 as illustrated by arrow "A" (FIG. 7A) into alignment with folded edge 116, with the edge 113 being allowed to fall back over the folded stack portion of the strip. This brings the strip into the form shown in FIG. 11A (which is the same form as FIG. 11 except that the drape is upside down relative to FIG. 11).

The stack is then folded back over as illustrated by the arrow "B" in FIG. 11A, with the edge 113 being allowed to fall back over the folded stack. This brings the drape into the form shown in FIGS. 14 and 15. The steps illustrated in FIGS. 7A and 11A eliminate the intermediate forms shown in FIGS. 8–9 and 12–13.

The drape 1 is now in the form in which it is supplied to the user. It may be packaged in this form, either as an individual item or together with other drapes. The folding procedure described involves fewer individual folds than would be required to bring the drape to a similar size using a conventional fan-folding procedure, and advantageously leaves one end (13) of the multi-length strip 8 exposed, to assist in subsequently unfolding the drape as described below.

Figure 16:
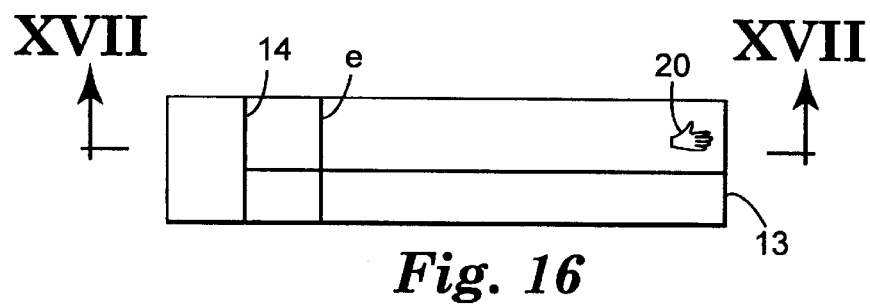
FIG. 16 is a plan view showing the drape after a first unfolding step or after an alternative fifth folding step.
Figure 17:
FIG. 17 is a diagrammatic cross-section on the line XVII—XVII in FIG. 16.

When the drape is to be unfolded to cover a table, the stack 18 is placed on the table with the end 13 uppermost and to the right of the stack (as viewed by the user). The distinctive marking 20 serves to indicate to the user that the stack 18 is in the correct orientation. The user now grasps the end 13 (comprising all layers of the multi-layer strip 8) and, while taking care not to touch the table on which the drape is located, pulls the end 13 to the right, away from the stack 18. This one action enables the user, using one hand only, to unfold one part of the multi-layer strip 8 completely, bringing the drape 1 to the form shown in FIGS. 16 and 17. It will be noted that the end 14 of the multi-layer strip 8 is now exposed. The user drops the end 13 and, still taking care not to touch the table on which the drape 1 is located, grasps the end 14 and pulls it to the left. This action enables the user, again using one hand only, to unfold the remainder of the multi-layer strip 8 thereby returning the latter to the form shown in FIG. 3.

It is now necessary for the user to open up the fan-folds described above with reference to FIGS. 1–3. To do that, the user places both hands under the flap 10 and pulls the drape towards him/herself This brings the drape back to the form shown in FIG. 2 and thereby covers the nearer part of the table. The user now places both hands under the flap 9 and pushes the remaining part of the drape away from him/herself to open up the drape completely and thereby cover the rest of the table. During the latter action, the user can lean forward and contact the nearer part of the table if necessary, since that part of the table is already protected by the drape.

The unfolding procedure described is comparatively straightforward, due particularly to the possibility of opening up the drape into the form shown in FIG. 3 in two simple, one-handed, actions.

Various modifications can be made to of the folding procedure described above. For example, the manner in which the drape is folded into the multi-layer strip 8 (FIG. 3) can be varied provided that it remains possible for the user to unfold the drape comparatively easily. The initial two steps in the folding of the multi-layer length 8 (FIGS. 5 and 6) can also be interchanged without affecting the remainder of the procedure A more substantially modified procedure, which can commence after the drape has been folded into the form shown in FIGS. 6 and 7, is illustrated diagrammatically in FIGS. 18 to 21 and can be summarised as follows:

(I) The folded edge 15 is folded back into alignment with the folded edge 16 bringing the drape into the form which resulted from the first unfolding step described above (FIG. 17).

Figure 18:
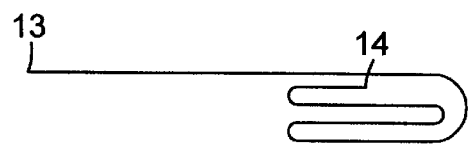
FIGS. 18 to 21 are diagrammatic cross-sections, similar to FIG. 17, illustrating the form of the drape after further alternative folding steps.

(II) The end 13 of the multi-layer strip 8 is folded over on the line e, concealing the end 14 (FIG. 18).

Figure 19:
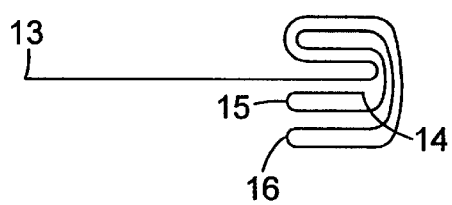
Figure 20:
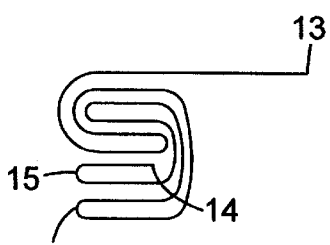
Figure 21:
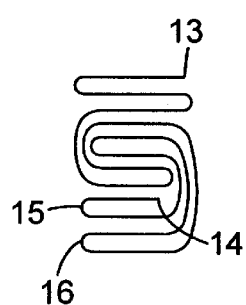

(III) The stack of folded material formed so far, comprising several thicknesses of the multi-layer strip 8, is folded in half (FIG. 19).

(IV) The end 13 is brought back over the top of the stack of folded material (FIG. 20) and is then fan-folded onto the top of the stack (FIG. 21), bringing the end 13 to the top of the stack as in FIG. 15 but with the remainder of the stack arranged somewhat differently.

This folding procedure is slightly more complex than that described by the steps (i) to (vi) above but permits the folded drape to be unfolded in a similar manner.

It will be appreciated that the folding procedures described above with reference to table drapes could be applied, where appropriate, to any sufficiently large rectangular drapes regardless of their intended purpose. The same folding procedures could, for example, be applied to patient drapes.

I claim:

1. A surgical drape comprising a rectangular sheet of drape material folded, prior to use, in one direction to form a multi-layer strip of material having first and second ends, and then in the orthogonal direction to form a stack of folded material with the first end of the multi-layer strip exposed at the top of the stack and the second end of the multi-layer strip contained within the stack, wherein at least one of the folds in the orthogonal direction extends through more than two layers of the multi-layer strip;

the folds in the orthogonal direction allowing a first part of the stack to be unfolded by pulling the first end in a first direction and the second end of the multi-layer strip being exposed by unfolding the first part of the stack;

the folds in the orthogonal direction allowing the stack to be unfolded by pulling the second end in a second direction, opposite to the first direction.

2. A surgical drape as claimed in claim 1, in which the first end of the multi-layer strip is generally aligned with one side of the stack.

3. A surgical drape as claimed in claim 2, in which the second end of the multi-layer strip is generally aligned with said one side of the stack.

4. A surgical drape as claimed in claim 1, in which the first end of the multi-layer strip is generally aligned with one side of the stack, and the folds in the orthogonal direction allow the first part of the stack to be unfolded by pulling the first end to that side of the stack.

5. A surgical drape as claimed in claim 1, in which the folds in said one direction comprise a first plurality of fan-folds from one side of the rectangular sheet to a central region of the sheet and a second plurality of fan-folds from the opposite side of the rectangular sheet to said central region.

6. A surgical drape according to claim 1 wherein at least one of the folds in the orthogonal direction extends through at least five layers of the multi-layer strip.

7. A surgical drape comprising a rectangular sheet of drape material folded, prior to use, in one direction to form a multi-layer strip of material having first and second ends, and then in the orthogonal direction to form a stack of folded material with the first end of the multi-layer strip exposed at the top of the stack and the second end located within the stack, wherein the folds in the orthogonal direction allow a first part of the stack to be unfolded, to expose the second end, by pulling the first end in a first direction.

8. A surgical drape as claimed in claim 7, in which the folds in the orthogonal direction allow the stack to be unfolded completely by pulling the second end in a second direction, opposite to the first direction.

9. A surgical drape as claimed in claim 7, in which the first and second ends of the multi-layer strip are generally aligned with one side of the stack.

10. A surgical drape as claimed in claim 7, in which the folds in said one direction comprise a first plurality of fan-folds from one side of the rectangular sheet to a central region of the sheet and a second plurality of fan-folds from the opposite side of the rectangular sheet to said central region.

11. A method of folding a rectangular surgical drape comprising the steps of:

folding the drape in one direction to form a multi-layer strip of material having first and second ends; and folding the multi-layer strip in the orthogonal direction to form a stack of folded material with the first end of the multi-layer length exposed at the top of the stack, wherein at least one of the folds in the orthogonal direction extends through more than two layers of the multi-layer strip.

12. A method as claimed in claim 11, in which the multi-layer length of material is folded from the second end first, to position the second end within the stack.

13. A method as claimed in claim 11, comprising positioning the first end on the top of the stack, in alignment with the second end.

14. A method as claimed in claim 11, in which the step of folding the drape in said one direction comprises forming a first plurality of fan-folds from one side of the rectangular sheet to a central region of the sheet and a second plurality of fan-folds from the opposite side of the rectangular sheet to said central region.

15. A method of folding a rectangular surgical drape comprising the steps of:

folding the drape in one direction to form a multi-layer strip of material having first and second ends; and folding the multi-layer strip in the orthogonal direction to form a stack of folded material with the first end of the multi-layer strip exposed at the top of the stack and the second end located within the stack, wherein the folds in the orthogonal direction allow a first part of the stack to be unfolded, to expose the second end, by pulling the first end in a first direction.

16. A method as claimed in claim 15, in which the multi-layer strip of material is folded from the second end first, to position the second end within the stack.

17. A method as claimed in claim 15, comprising positioning the first and second ends in alignment with one side of the stack.

18. A method of using a surgical drape, comprising the steps of:

providing a surgical drape comprising a rectangular sheet of drape material folded in one direction to form a multi-layer strip of material having first and second ends, and then in the orthogonal direction to form a stack of folded material with the first end of the multi-layer strip exposed at the top of the stack and the second end located within the stack;

placing the folded drape on a surface to be covered with the first end of the multi-layer strip exposed without having unfolded any portion of the drape to expose the first end;

unfolding a first part of the stack, to expose the second end of the multi-layer strip, by pulling the first end in a first direction;

unfolding the remainder of the stack by pulling the second end in a second direction opposite to the first direction; and unfolding the multi-layer strip of material in directions perpendicular to the first and second directions.

* * * * *